United States Patent [19]

Culler

[11] Patent Number: 4,673,354
[45] Date of Patent: Jun. 16, 1987

[54] STABLE SILANOL PRIMING SOLUTION FOR USE IN DENTISTRY

[75] Inventor: Scott R. Culler, St. Paul, Minn.

[73] Assignee: Minnesota Mining and Manufacturing Company, St. Paul, Minn.

[21] Appl. No.: 782,428

[22] Filed: Oct. 1, 1985

[51] Int. Cl.$^4$ ............................................. A61C 5/00
[52] U.S. Cl. ................................. 433/217.1; 106/35; 106/287.14; 106/287.15; 106/287.16; 427/2
[58] Field of Search .......... 433/217.1; 106/35, 287.14, 106/287.15, 287.16; 427/2

[56] References Cited

U.S. PATENT DOCUMENTS

| | | | |
|---|---|---|---|
| 3,369,297 | 2/1968 | Halpern et al. | 32/2 |
| 3,423,828 | 1/1969 | Halpern et al. | 32/8 |
| 3,423,829 | 1/1969 | Halpern et al. | 32/8 |
| 3,423,830 | 1/1969 | Halpern et al. | 32/8 |
| 3,423,831 | 1/1969 | Semmelman | 32/8 |
| 3,976,497 | 8/1976 | Clark | 106/287 SE |
| 3,986,997 | 10/1976 | Clark | 260/29.2 M |
| 4,053,496 | 10/1977 | Fory et al. | 260/448.8 R |
| 4,101,513 | 7/1978 | Fox et al. | 526/193 |
| 4,113,665 | 9/1978 | Law et al. | 528/29 |
| 4,117,595 | 10/1978 | Ibsen et al. | 32/8 |
| 4,195,141 | 3/1980 | Buning et al. | 525/328 |
| 4,200,980 | 5/1980 | Johnston | 433/8 |
| 4,247,436 | 1/1981 | Buning et al. | 260/29.6 H |
| 4,256,603 | 3/1981 | Ibsen et al. | 252/182 |
| 4,294,349 | 10/1981 | Ibsen et al. | 206/63.5 |
| 4,341,213 | 7/1982 | Cohen | 128/284 |
| 4,352,894 | 10/1982 | Schmidt | 521/91 |
| 4,356,233 | 10/1982 | Lange et al. | 428/336 |
| 4,368,313 | 1/1983 | Hayes | 528/14 |
| 4,370,439 | 1/1983 | Melle et al. | 524/513 |
| 4,396,650 | 8/1983 | Lange et al. | 427/409 |
| 4,435,219 | 3/1984 | Greigger | 106/287.16 |
| 4,439,239 | 3/1984 | Greigger et al. | 528/12 |
| 4,464,450 | 8/1984 | Teuscher | 430/59 |

OTHER PUBLICATIONS

Pluddemann, "Silane Coupling Agents", Ch. 3, 49–73 (New York, 1982).
Instruction Sheets for the "Fusion", Silanit, Kerr and Den-Mat Commercial Products.
Lee, "Wettability of Organosilanes. I. Wettability and Conformation of Reactive Polysiloxanes on Silicate Glass Surface", *Soc. Plastic Ind.*, sec. 9D, pp. 1–14 (1968).
Rosen, "From Treating Solution to Filler Surface and Beyond", *J. Coating Technology*, 50, 70–82 (1978).
Semmelman et al., "Silane Bonding Porcelain Teeth to Acrylic", *J.A.D.A.*, 76, 69–73 (1968).
Lee, "Wettability and Conformation of Reactive Polysiloxanes", *J. Colloid and Interface Science*, 27(4), 751–760 (1968).

*Primary Examiner*—Lorenzo B. Hayes
*Attorney, Agent, or Firm*—Donald M. Sell; James A. Smith; David R. Cleveland

[57] ABSTRACT

A method for priming a dental material using a liquid layer of acidic, non-hazy silanol priming solution containing substantially fully hydrolyzed organofunctional silanol, water, and volatile alcohol or ketone solvent. The compositions contain a sufficiently low amount of silanol and sufficiently high amounts of solvent and acid to have a priming strength in excess of the cohesive strength of dental porcelain after storage of the solution at room temperature for at least about 45 days.

22 Claims, No Drawings

STABLE SILANOL PRIMING SOLUTION FOR USE IN DENTISTRY

TECHNICAL FIELD

This invention relates to a method for priming dental materials with silanol solutions, to dental materials treated with such solutions, and to silanol priming solutions for use in dentistry.

BACKGROUND ART

Silane or silanol priming solutions have been used for many years for priming and repair of dental materials such as porcelain, metals, alloys and dental composites. These primers typically are sold as two-part products which are mixed together prior to use, or as one-part products which are used as is.

Representative two-part products include "Fusion" liquid surface primer (George Taub Products and Fusion Co., Inc.) and "Silanit" porcelain repair material (Vivadent). The "A" portion of the Fusion product appears to be approximately an 85:15 weight percent water:isopropanol solution with a pH of 4.7, and the "B" portion appears to be approximately 12 to 15 weight percent gamma-methacryloxypropy/trimethoxysilane dissolved in isopropanol. Equal volumes of the A and B portions are mixed together and allowed to stand for 15 minutes prior to use, forming a clear silanol solution containing approximately 43:50-52:6-8 weight percent water:isopropanol:silanol. The mixture is said by the manufacturer to be stable for about three weeks after mixing if stored under refrigeration or in a cool dark area. After that time the mixture becomes cloudy (due to solution condensation of the hydrolyzed silanol to form insoluble dimer, oligomer, or polymer) and must be discarded.

The "A" portion of the Silanit product appears to be approximately a 56:44 weight percent water:isopropanol solution with a pH of 4.6, and the "B" portion appears to be substantially pure gamma-methacryloxypropyltrimethoxysilane. The A and B portions are mixed together in a 5:1 ratio and allowed to stand for 15 minutes prior to use, forming a clear silanol solution containing approximately 47:37:17 weight percent water:isopropanol:silanol. The mixture is said by the manufacturer to be usable for about 24 hours after mixing. After that time the mixture becomes cloudy and must be discarded.

Representative one-part products include "Kerr" porcelain repair primer (Sybron Corp.) and "Den-Mat" porcelain repair bonding agent (Den-Mat Corporation). The Kerr product appears to be approximately 5 weight percent gamma-methacryloxypropyltrimethoxysilane dissolved in ethanol. This product also appears to contain about 0.4 weight percent water (as measured by Karl Fischer analysis) and has a pH of about 6.8. The Den-Mat product is described in U.S. Pat. Nos. 4,117,595, 4,256,603 and 4,294,349, and appears to be a mixture of approximately 5 weight percent gamma-methacryloxypropyltrimethoxysilane and 2.5 weight percent gamma-glycidoxypropyltrimethoxysilane in n-butanol. Each of these one-part products contains essentially completely unhydrolyzed silane when in solution. Each is applied to an acid-treated substrate and allowed to stand while the silane hydrolyzes in situ due to the action of acid and adventitious moisture.

Other silane or silanol priming solutions for use in dentistry are described in U.S. Pat. Nos. 3,369,297, 3,423,828, 3,423,829, 3,423,830, 3,423,831, 4,200,980, and in Semmelman et al., "Silane bonding Porcelain Teeth to Acrylic", *J.A.D.A.*, 76, 69–73 (1968). Properties of silane and silanol solutions in general are discussed in Lee, "Wettability and Conformation of Reactive Polysiloxanes", *J. Colloid and Interface Science*, 27(4), 751-760 (1968), Lee, "Wettability of Organosilanes. I. Wettability and Conformation of Reactive Polysiloxanes on Silicate Glass Surface", *Soc. Plastic Ind.*, sec. 9D, pp. 1–14 (1968), Rosen, "From Treating Solution to Filler Surface and Beyond", *J. Coating Technology*, 50, 70–82 (1978), and Pluddemann, "Silane Coupling Agents", Ch.3, 49–73 (New York, 1982). Other patents relating to silane or silanol solutions include U.S. Pat. Nos. 3,976,497, 3,986,997, 4,101,513, 4,113,665, 4,195,141, 4,247,436, 4,341,213, 4,352,894, 4,368,313, 4,370,439, 4,396,650, 4,435,219 and 4,439,239.

SUMMARY OF THE INVENTION

Ideally, a silane or silanol priming solution should be fully hydrolyzed while in solution, that is, substantially all of its hydrolyzable groups should be converted to silanol (SiOH) groups. If the priming solution is incompletely hydrolyzed, then after being coated upon a substrate and dried it will not bond to the substrate to the fullest possible extent. Unfortunately, increasing the degree of hydrolysis in solution also increases the tendency for the silanol groups to undergo solution condensation and for the priming solution to become hazy. When this occurs, its ability to prime porcelain decreases drastically.

If used according to directions, the above-mentioned commercial priming solutions often are not fully hydrolyzed. For example, for the two-part products the 15 minute standing time after mixing is inadequate to ensure full hydrolysis at room temperature. At that time the Fusion and Silanit products are only 93% and 60% hydrolyzed, respectively, as measured using infrared ("IR") absorption analysis. Longer standing times (on the order of one hour or more for the Fusion product at room temperature if no agitation during standing is employed, and longer for the Silanit product) are required to obtain full hydrolysis. Any standing time is something of an inconvenience, since meanwhile both patient and dentist may be kept waiting. For the one-part products, the degree of hydrolysis depends on technique, ambient humidity, and the amount of moisture and acid present on the substrate. This results in a poorly controlled, and possibly incomplete, degree of hydrolysis.

In addition to their other deficiencies, the above-described commercial products contain unnecessarily high levels of silane. For the two-part products, the high silane level detracts from storage stability after mixing. For both the one-part and two-part products, the high silane level represents a waste of silane. Silanes are very effective primers if fully hydrolyzed in solution and properly applied, and good priming and adhesion could be obtained with less silane than is present in the above-described commercial products.

The present invention provides, in one aspect, a method for priming a dental material comprising the steps of (A) applying to said material a liquid layer of acidic, non-hazy, silanol priming solution comprising (i) substantially fully hydrolyzed organofunctional silanol, (ii) water, and (iii) volatile alcohol or ketone solvent, said solvent being miscible with water in all proportions, having between two and four carbon atoms, and having a boiling point between about 50° and 125° C., said solution containing a sufficiently low amount of silanol and sufficiently high amounts of solvent and acid to have a priming strength in excess of the cohesive strength of dental porcelain after storage of said solution at room temperature for at least about 45 days, and (B) allowing said layer to dry. The present invention also provides dental articles, suitable for use in the mouth, comprising a dental material having thereon a liquid layer of said solution. In addition, the present invention provides one-part liquid silanol priming compositions comprising said solution and containing ethanol as solvent.

In comparison to the above-mentioned two-part products, the preferred compositions of the invention are easier to use, require no standing time, typically are more fully hydrolyzed, have better adhesion to porcelain and metals, and have better storage stability. In comparison to the above-mentioned one-part products, the preferred compositions of the invention are typically more fully hydrolyzed and less technique sensitive, and have substantially improved adhesion to metals.

DETAILED DESCRIPTION

As used herein, the term "dental materials" refers to dental porcelain, dental alloys, and cured dental composites, restoratives and adhesives, such materials being suitable for use in the oral environment. The silanol priming solution is "non-hazy", that is, it is substantially clear in appearance and is thus substantially free of insoluble dimer, oligomer or polymer formed by solution condensation of silanol molecules. A convenient test for evaluating whether or not a solution is non-hazy can be performed by placing a freshly shaken sample of the solution in a glass vessel with at least a 40 mm inside diameter (e.g. a 125 ml cylindrical glass jar, 125 ml "French Square" glass jar, or 100 ml "Pyrex" beaker) and holding a sheet of paper bearing a message with letters at least as large as ten pitch type behind the vessel. If the message is legible through the solution, then the solution is non-hazy. When evaluated using a laboratory spectrophotometer, a non-hazy solution will transmit at least about 98% of the light transmitted by distilled water at a peak wavelength of 650 nm and a path length of 1 cm.

Freedom from haze has heretofore been used as a benchmark test for the presence of monomeric silanol and the absence of dimer, oligomer or polymer formed by solution condensation of silanol molecules (see, e.g., the Pluddemann reference cited above). By hydrolyzing and dehydrating gamma-methacryloxypropyltrimethoxysilane to convert it to an oligomeric silanol condensate, and adding such condensate to the solvents used in the present invention, it was found that such solvents are capable of dissolving appreciable quantities of oligomeric silanol condensate without loss of solution clarity. Once dissolved, such oligomeric silanol condensates are very difficult to detect using conventional spectrographic or chromatographic analytical techniques. However, clear solutions containing such condensates exhibit very poor porcelain priming strength. Accordingly, both freedom from haze and porcelain priming strength are evaluated to determine whether or not the silanol priming solutions of the invention are substantially free of soluble and insoluble silanol condensates.

As indicated above, the silanol priming solution has a priming strength in excess of the cohesive strength of dental porcelain after storage of the solution at room temperature for at least about 45 days. Priming strength is evaluated using the porcelain bonding procedure described below in run no. 1 of EXAMPLE 6, with a "priming strength in excess of the cohesive strength of dental porcelain" referring to the occurrence of cohesive failure in at least four out of five porcelain samples tested in such procedure. For brevity, the term "storage stable" will refer to silanol priming solutions exhibiting such priming strength after room temperature storage of the silanol priming solution for a desired period of time. If the solution becomes hazy during storage then it is not necessary to evaluate its priming strength, since haze is a reliable indicator of loss of priming strength. If the solution remains clear during storage, then its priming strength should be evaluated to determine whether or not the solution is storage stable.

Preferably, the compositions of the invention are storage stable for at least about three to six months or more, more preferably at least about one year or more. Elevated temperature storage stability is also a useful guide to room temperature storage stability, with 10 days of 45° C. storage stability corresponding to about 40 days of room temperature storage stability.

The organofunctional silanol in the compositions of the invention is an organofunctional silane compound containing at least one OH group and containing at least one non-hydrolyzable polymerizable organic group, both such groups being bonded to a silicon atom. Most preferably, the silanol is monomeric, that is, containing one silicon atom. Suitable polymerizable organic groups include vinyl, acryl, methacryl, glycidyl, allyl and styryl groups. Acryl and methacryl groups are preferred. Preferred silanols have the formula $R_nSi(OH)_{4-n}$ wherein R is a polymerizable organic group of the type described above and n is one to three, most preferably one.

It is convenient to form the silanol by hydrolysis of an organofunctional hydrolyzable silane using a stoichiometric excess of water. Preferred hydrolyzable silanes have the formula $R_nSiX_{4-n}$ wherein R and n are as defined above and X is a hydrolyzable labile group. Suitable labile groups include alkoxy, substituted alkoxy, acyloxy, substituted acyloxy, and halogen. Alkoxy labile groups are preferred, and methoxy and ethoxy labile groups are most preferred. Preferably, the organofunctional hydrolyzable silane is substantially free of amine groups, since silanols formed therefrom tend to polymerize spontaneously in water solution.

The silanol is substantially "fully hydrolyzed", that is, it is substantially free of hydrolyzable labile groups. A useful test for full hydrolysis can be performed using IR analysis, with full hydrolysis being indicated by an absence of the characteristic absorption band formed by any hydrolyzable labile groups (e.g., alkoxy groups). For example, for methoxy silane groups the absorption band at 2842 cm$^{-1}$ disappears during hydrolysis. Normalization to other absorption bands (e.g., the C=C absorption band at 1635–1640 cm$^{-1}$ contained in unsaturated silanes) enables the degree of hydrolysis to be quantified.

Suitable hydrolyzable silanes which can be used to make the silanols contain at least one non-hydrolyzable polymerizable organic group, and include silanes such as acrylato silanes, methyacrylato silanes, mercapto silanes, and epoxy silanes. Commercially available hydrolyzable silanes include "A-151" vinyltriethoxysilane, "A-172" vinyltri(2-methoxyethoxy)silane, "A-174" gamma-methacryloxypropyltrimethoxysilane, "A-186" 3,4-epoxycyclohexylmethyltrimethoxysilane, "A-187" gamma-glycidoxypropyltrimethoxysilane, and "A-189" gamma-mercaptopropyltrimethoxysilane (all commercially available from Union Carbide Corp.), "Z-6030" gamma-methacryloxypropyltrimethoxysilane, "Z-6040" gamma-glycidoxypropyltrimethoxysilane, and "XZ-8-0951" gamma-mercactopropyltrimethoxysilane (all commercially available from Dow Corning Corp.), "A0564" allyltriethoxysilane, "D4050" diallyldichlorosilane, "D6205" divinyldiethoxysilane, "G6720" glycidoxypropyltriethoxysilane, "M8542" methacryloxypropyl-dimethylchlorosilane, and "S1588" m,p-styrylethyltrimethoxysilane (all commercially available from Petrarch Systems, Inc.), and mixtures thereof. Gamma-methacryloxypropyltrimethoxysilane is a preferred hydrolyzable silane.

The silanol is present in compositions of the invention in an amount sufficient to provide the desired degree of silane priming when the composition is applied to a substrate, coincident with attainment of storage stability for a desired period of time. In general, the amount of silanol required to obtain good priming strength can be much less than the amounts of silane employed in existing commercial dental silane primers. Increased amounts of silanol will detract from storage stability. A preferred amount of silanol is about 0.01 to about nine weight percent, more preferably about 0.05 to about five weight percent, and most preferably about 0.5 to about 1.5 weight percent, based on the total weight of the composition.

The water which is present in compositions of the invention preferably is substantially free of fluoride, bases, and other contaminants which could promote solution condensation of the silanol. Deionized water is preferred. For compositions of the invention prepared by reacting a stoichiometric excess of water with a hydrolyzable silane, the excess water conveniently serves as the source of water in such compositions. To maximize storage stability, it is preferred that the water be acidified with a water-soluble acid before the water is combined with the remaining ingredients of the composition. A preferred pH range for the water is about two to about six, more preferably about three to about five. Suitable water-soluble acids preferably are sufficiently volatile to permit their substantial removal by evaporation from a brush-applied film of a composition of the invention within about ten minutes after application of the film to a dry substrate at room temperature and pressure. Preferred water-soluble acids are organic acids which can be used in the oral environment and include formic acid, acetic acid, trifluoroacetic acid, propionic acid, pentafluoropropionic acid, heptafluorobutyric acid, and mixtures thereof. Mineral acids or nonvolatile organic acids such as hydrochloric acid, nitric acid, sulfuric acid, phosphoric acid, lactic acid, citric acid and tartaric acid can also be used, but they preferably are removed with a water rinse after the composition of the invention is applied and dried. Acetic acid is a preferred water-soluble acid.

The volatile solvent in the compositions of the invention is an alcohol or ketone which is miscible with water in all proportions, that is, it forms a single phase solution when combined with water at any mixing ratio. Co-solvents can be used if desired to assure that the solvent is water-miscible. The solvent is sufficiently volatile to permit its substantial removal from a brush-applied film of a composition of the invention within about ten minutes after application of the film to a dry substrate at room temperature and pressure. Preferably, the solvent evaporates from such film within about five minutes, more preferably within one minute or less. Preferred solvents have a boiling point below about 100° C., most preferably below about 80° C. The solvent preferably does not promote solution condensation of the silanol and preferably is a solvent for the dimer of the silanol, in order to avoid depletion of silanol in the compositions of the invention. Alcohols are a preferred solvent. Ranked in descending order of preference, specific preferred solvents include ethanol (b.p. 78.5° C.), n-propanol (b.p. 97.4° C.), isopropanol (b.p. 82.4° C.), tert-butanol (b.p. 82.2° C.), 2-methoxyethanol ("Methyl Cellosolve", b.p. 125° C., commercially available from Union Carbide Corp.), and acetone (b.p. 56.5° C.). Mixtures of solvents can be used if desired. Ethanol appears to provide substantially better storage stability than other solvents. In addition, ethanol, n-propanol and isopropanol all appear to provide better storage stability than methanol, a substance which has previously been said to enhance stability of silanol solutions (see the Rosen and Pluddemann references referred to above). Although it is produced in small amounts by the hydrolysis of methoxysilanes, the use in this invention of any substantial amount of methanol as solvent is contraindicated due in part to its retinopathy.

It should be noted in passing that many of the solvents used in the present invention have been referred to heretofore in various prior art references as solvents for silanes or silanols. However, the compositions shown in such references typically have not contained all of the ingredients (e.g., acid, fully hydrolyzed silanol, or water) present in the silanol priming solutions of this invention. In addition, where fully hydrolyzed silanol solutions are referred to in such references, their stability typically is said to be limited to a few hours or days.

As indicated above, the compositions of the invention contain sufficient solvent to have at least about 45 days of storage stability. The desired amount of solvent primarily will depend upon the particular solvent chosen, the amount of water, and the amount and type of silanol employed. As the ratio of solvent to water is increased, storage stability increases. Increased amounts of silanol generally require an increase in the solvent:water ratio. Silanol priming solutions containing the preferred solvent ethanol preferably contain at least 35 weight percent ethanol. More preferably, such compositions contain at least about 50 weight percent ethanol and most preferably about 70 to about 99 weight percent ethanol. For other solvents, the silanol priming solutions preferably contain at least about 50 weight percent of solvents such as n-propanol and isopropanol, at least about 60 weight percent of a solvent such as tert-butanol, and at least about 70 weight percent of solvents such as 2-methoxyethanol and acetone. Larger amounts of such other solvents can be used if desired.

Preferably, the solvent is mixed with a water-soluble acid before the solvent is combined with the remaining ingredients of the composition. Suitable water-soluble acids include those already mentioned above.

As indicated above, the compositions of the invention contain sufficient acid to have at least about 45 days of storage stability. The desired amount of acid will depend primarily upon the amount of water and the amount and type of silanol employed. Increased amounts of water or silanol generally require an increase in the amount of acid. Expressed in terms of pH, the silanol priming solutions preferably have a pH below about six, more preferably about two to about six, and most preferably about three to about five.

The compositions of the invention conveniently are prepared by first combining acid, water and solvent in any order. Next, the precursor hydrolyzable silane is added with rapid agitation for a time e.g., one hour or more) sufficient to ensure that the silane becomes substantially fully hydrolyzed. An emulsifier can be used if desired to accelerate hydrolysis. If desired, adjuvants such as wetting aids, surfactants, indicators, dyes, thixotropes, and the like can also be added to compositions of the invention. The amounts and types of such adjuvants will be apparent to those skilled in the art.

Compositions of the invention can be put up in conventional packaging (e.g., bottles of glass or plastic, syringes, ampoules, and the like). Preferably, the packaging provides a substantially hermetic seal to minimize evaporation of the solvent. Many commercially practical packages will permit a small quantity of solvent to evaporate during storage, and this should be compensated for if such packaging is employed.

The compositions of the invention can be used in any dental application where silane priming solutions have hitherto been employed. Such solutions typically are used in the mouth, for example to prime dental materials such as dental porcelain (e.g., feldspathetic, nepheline syenite, alumina-base and synthetic porcelains), dental metals and alloys (e.g., metals or alloys of gold, silver, platinum, palladium, chromium, and nickel) and cured dental composites, restoratives and adhesives. A particularly preferred application is the repair of crowns and bridgework, especially where bonds to dental porcelain, metals or alloys must be made. The compositions of the invention can also be used in conventional silane priming applications if desired (e.g., the priming of particulate or fibrous fillers for composites, such as fumed silica particles and "E-Glass" and "Fiberglas" fibers).

Following application of a composition of the invention to a desired substrate, the solvent and water are permitted to evaporate. If desired, a drying agent can be used to speed evaporation. Coincident with such evaporation surface condensation of the silanol begins. The resulting primed substrate exhibits enhanced adhesion to polymerizable resins. The primed substrate can be coated with a layer or layers of polymerizable unfilled dental adhesive and overcoated with a layer or layers of filled dental composite or restorative, in order to alter the shape of the substrate (e.g., to restore the shape of the cusp of a crown). The primed substrate also can be coated with a layer or layers of unfilled dental adhesive and overcoated with a layer or layers of filled dental adhesive, then mated with a second primed, dental adhesive-coated substrate (e.g., to cement together the pieces of a broken crown or bridge). Standard analysis techniques can be employed to examine the hydrolytic stability and effectiveness of the priming treatment (e.g., water immersion or thermocycling of bonded samples, followed by tensile or shear bond strength measurements).

The excellent storage stability, substantially complete hydrolysis, and freedom from mixing of the compositions of the invention minimizes waste of materials and time spent by the dentist, and makes the compositions relatively insensitive to technique, surface moisture and ambient humidity. These advantages also aid in fabrication of better crown and bridge repairs while minimizing chair time and patient recalls.

The following examples are offered to aid understanding of the present invention and are not to be construed as limiting the scope thereof. Unless otherwise indicated, all parts and percentages are on a weight basis.

EXAMPLE 1

In a series of 21 runs, varying amounts of absolute ethanol were mixed with sufficient glacial acetic acid to give an electrically measured pH of 4.7, varying amounts of deionized water were acidified to pH 3.5 with glacial acetic acid, and the acidified water and ethanol then combined in glass vessels. One percent "A-174" silane was added to the water/ethanol solutions. The solutions were mixed for one hour. The resulting silanol priming solutions had a pH between 3.5 and 4.7. Full hydrolysis of silane to silanol (as evaluated using IR analysis) occurred in all solutions. The glass vessels were securely capped, stored at room temperature and observed periodically to determine when each priming solution became hazy. Haze formation was evaluated by viewing a sheet of paper bearing a printed message (the phrase "Can you read this?" in letters written four to five millimeters high) through a 225 ml glass bottle containing 20 grams of the priming solution. The priming solution was regarded as non-hazy if the printed message remained legible. In some instances, the priming solution underwent a transition from non-haziness to haziness over the course of one or more days. In such instances, the priming solution was identified as being slightly hazy during the transition period.

Set out below in TABLE I are the run number, percent solvent in the priming solution, number of days during which the priming solution remained non-hazy and elapsed time to the onset of slight haze or haze.

TABLE I

| Run no. | % Solvent | No. of days non-hazy | Elapsed time to onset of slight haze or haze, days | |
| --- | --- | --- | --- | --- |
| | | | Slight haze | Haze |
| 1 | 99 | >115 | — | — |
| 2 | 94 | >115 | — | — |
| 3 | 89 | >115 | — | — |
| 4 | 84 | >115 | — | — |
| 5 | 79 | >115 | — | — |
| 6 | 74 | >115 | — | — |
| 7 | 69 | >115 | — | — |
| 8 | 64 | >115 | — | — |
| 9 | 59 | >115 | — | — |
| 10 | 54 | >115 | — | — |
| 11 | 49 | >115 | — | — |
| 12 | 44 | >115 | — | — |
| 13 | 39 | >115 | — | — |
| 14 | 34 | 42 | 43 | 54 |
| 15 | 29 | 24 | 25 | 32 |
| 16 | 24 | 24 | 25 | 32 |
| 17 | 19 | 9 | 10 | 24 |
| 18 | 14 | 6 | 7 | 9 |
| 19 | 9 | 6 | 7 | 9 |
| 20 | 4 | 6 | — | 7 |
| 21 | 0 | 6 | — | 7 |

This example shows that priming solutions of the invention containing more than 34 percent ethanol remained non-hazy for more than three months. The porcelain priming strength of several of the above priming solutions (those of run nos. 1, 11 through 13, 20 and 21) was evaluated using the procedure of run no. 1 of EX- AMPLE 6. The priming solutions of run nos. 20 and 21 failed adhesively. Each of the remaining tested priming solutions had a priming strength in excess of the cohesive strength of dental porcelain, and thus was storage stable for at least three months.

EXAMPLE 2

In a series of 23 runs, the pH of the priming solution of run no. 6 of EXAMPLE 1 was varied (by adding or removing glacial acetic acid) by units of about 0.2 pH between pH 1.99 and pH 7.35. Set out below in TABLE II are the run number and pH of each priming solution.

TABLE II

| Run no. | pH |
| --- | --- |
| 1 | 1.99 |
| 2 | 2.20 |
| 3 | 2.42 |
| 4 | 2.59 |
| 5 | 2.81 |
| 6 | 2.99 |
| 7 | 3.21 |
| 8 | 3.41 |
| 9 | 3.60 |
| 10 | 3.80 |
| 11 | 4.00 |
| 12 | 4.18 |
| 13 | 4.42 |
| 14 | 4.62 |
| 15 | 4.82 |
| 16 | 5.01 |
| 17 | 5.23 |
| 18 | 5.40 |
| 19 | 5.61 |
| 20 | 5.80 |
| 21 | 6.05 |
| 22 | 6.22 |
| 23 | 7.35 |

Each of the priming solutions was fully hydrolyzed (as measured using IR analysis) and remained non-hazy for over 45 days when stored at room temperature. However, evaluation of the priming solutions of run nos. 1, 6, 11, 16–21 and 23 indicated that only priming solutions with a pH below 6.05 had a priming strength exceeding the cohesive strength of dental porcelain.

This example illustrates several priming solution of the invention which are storage stable for at least 45 days over a wide range of pH values, and several compositions (pH 6.05 and above) which are not storage stable despite remaining non-hazy during storage.

EXAMPLE 3

In a series of 20 runs, priming solutions containing varying amounts of A-174 silane, varying amounts of ethanol, and 25 precent deionized water were prepared using the method of EXAMPLE 1. Set out below in TABLE III are the run no., precent solvent in the priming solution, percent silane used to form the silanol in the priming solution, number of days during which the priming solution remained non-hazy and elapsed time to the onset of slight haze or haze.

TABLE III

| Run no. | % Solvent | % Silane | No. of days non-hazy | Elapsed time to onset of Slight haze or haze, days | |
| --- | --- | --- | --- | --- | --- |
| | | | | Slight haze | Haze |
| 1 | 74 | 1 | >45 | — | — |
| 2 | 73 | 2 | >45 | — | — |
| 3 | 72 | 3 | >45 | — | — |
| 4 | 71 | 4 | >45 | — | — |
| 5 | 70 | 5 | >45 | — | — |
| 6 | 69 | 6 | >45 | — | — |
| 7 | 68 | 7 | >45 | — | — |
| 8 | 67 | 8 | >45 | — | — |
| 9 | 66 | 9 | >45 | — | — |
| 10 | 65 | 10 | >45 | — | — |
| 11 | 64 | 11 | >45 | — | — |
| 12 | 63 | 12 | 14 | 15 | 18 |
| 13 | 62 | 13 | 14 | 15 | 18 |
| 14 | 61 | 14 | 10 | 11 | 14 |
| 15 | 60 | 15 | 10 | 11 | 14 |
| 16 | 59 | 16 | 6 | 7 | 8 |
| 17 | 58 | 17 | 6 | 7 | 8 |
| 18 | 57 | 18 | 6 | 6 | 7 |
| 19 | 56 | 19 | 6 | 6 | 7 |
| 20 | 55 | 20 | 6 | 6 | 7 |

The priming solution prepared using one to 11 precent silane remained non-hazy for over 45 days at room temperature. Most or all of the priming solutions prepared from more than 11 percent silane (equivalent to about nine percent silanol) could have been made non-hazy for at least 45 days if a higher solvent:water ratio had been employed. Evaluation of the priming solutions of run nos. 2, 4, 6, 8 and 11 indicated that each had a priming strength exceeding the cohesive strength of dental porcelain.

This example illustrates priming solutions of the invention which are storage stable for at least 45 days over a wide range of silanol levels.

EXAMPLE 4

In a series of runs, the silanes "A-151", "A-172", "A-186", "A-196", and "G-6720" were substituted for "A-174" silane in the priming solution of run no. 6 of EXAMPLE 1. Each of the resulting priming solutions was non-hazy for over 45 days at room temperature. After storage, the priming solution prepared from A-151 silane had a priming strength in excess of the cohesive strength of dental porclain. The remaining priming solutions failed adhesively, indicating that the amounts of silanol and other ingredients in these compositions required further adjustment.

This example illustrates the use of a variety of silanols in priming solutions of the invention.

EXAMPLE 5

Using the method of EXAMPLE 1, five priming solutions were prepared using varying amounts of deionized water, ethanol, and A-174 silane. IR measurements indicated that each priming solution contained fully hydrolyzed silanol. The priming solutions were stored at room temperature and observed periodically. Set out below in TABLE IV are the run number, percent water and percent solvent in the priming solution, percent silane used to prepare the priming solution, and the pH of each priming solution.

TABLE IV

| Run no. | % Water | % Solvent | % Silane | pH |
| --- | --- | --- | --- | --- |
| 1 | 0.3 | 99.6 | 0.1 | 8.21 |
| 2 | 1.5 | 98.0 | 0.5 | 7.84 |
| 3 | 3.0 | 96.0 | 1.0 | 4.57 |
| 4 | 3.0 | 96.0 | 1.0 | 9.25 |
| 5 | 15.0 | 80.0 | 5.0 | 6.71 |

After over eleven months, priming solutions of run nos. 1, 2, 4 and 5 remained non-hazy. The priming solution of run no. 3 was prepared later than the other runs; after over nine months it remained non-hazy. If the ethanol was excluded, all of the priming solutions became hazy within six days. Evaluation of the priming solutions of run nos. 1–5 indicated that only the priming solution of run no. 3 had a priming strength exceeding the cohesive strength of dental porcelain.

The priming solution of run no. 3 was stored at 5°, 45° and 60° C. to determine its refrigerated and elevated temperature aging characteristics. After over nine months, it remained non-hazy. Evaluation of the priming strength of the samples stored at 45° and 60° C. indicated that the priming strength of each sample continued to exceed the cohesive strength of dental porcelain after storage. The priming solution of run no. 3 thus had outstanding storage stability. If stored in a tightly sealed container, it should be storage stable for several years at room temperature.

EXAMPLE 6

In a series of 14 runs, five samples each of a standard dental porcelain and a variety of semi-precious and non-precious dental alloys were partially embedded in cylindrical acrylic disks. The exposed portion of each sample was ground flat and parallel to the disk using a series of successively finer abrasive disks with final polishing using a 600 grit abrasive disk. The polished surfaces were cleaned using a 60 second etch with gelled 37% orthophosphoric acid, rinsed with distilled water and dried with oil-free air. A thin layer of the silanol priming solution of run no. 3 of EXAMPLE 5 was brushed onto the dried surface and blown dry with oil-free air. After the film lost its glossy appearance it was overcoated with a dental adhesive ("Light Cured Scotchbond" dental adhesive, 3M). The dental adhesive was cured using a ten second irradiation from a hand-held dental curing light ("Visilux" curing light, 3M). A previously prepared mold made from a 2.5 mm thick "Teflon" sheet with a five mm diameter hole through the sheet was lined by placing a gelatin sleeve in the hole, and clamped to the polished sample so that the central axis of the hole in the mold was normal to the polished, dental adhesive-coated sample surface. The hole in the mold was filled with a visible light-cure dental restorative ("Silux" brand, universal shade, 3M) and cured using a 20 second irradiation from the curing light. The sample and mold were allowed to stand for about ten minutes at room temperature, then stored in distilled water at 37° C. for 24 hours. The mold was then carefully removed from the sample leaving a button-like molded plug of restorative attached to the sample surface.

Adhesive strength was evaluated by mounting the acrylic disk in a holder clamped in the jaws of an "Instron" apparatus, with the polished sample surface oriented parallel to the direction of pull. A loop of orthodontic wire (0.44 diameter) was placed around the restorative button adjacent to the polished sample surface. The ends of the orthodontic wire were clamped in the pulling jaws of the Instron apparatus, thereby placing the bond in shear stress, and pulled at a crosshead speed of two mm/min until failure of the porcelain, adhesive bond, or restorative occurred.

In a first set of comparison runs, the procedure was repeated without use of the silanol priming solution. In a second set of comparison runs, the procedure was repeated using the "Kerr" etching agent and one-part "Kerr" silane primer referred to above, overcoating the primer with "Kerr Command Bond" dental adhesive, and placing "Kerr Command Ultra-Fine" restorative in the Teflon mold.

Set out below in TABLE V are the run number, sample substrate, and the average measured shear strengths obtained using the silanol primer of the invention, omitting it, and using the comparison silane primer.

TABLE V

| Run no. | Substrate | Shear strength, kg/cm2 | | |
|---|---|---|---|---|
| | | With silanol primer | Without silanol primer | With comparison silane primer |
| 1 | dental porcelain[1] | 135.8* | 88.4** | 177.5* |
| 2 | dental porcelain[1,2] | 172.1* | — | 161.7* |
| 3 | dental porcelain[1,3] | 189.1* | — | 149.0* |
| 4 | "Stroma"[4] | 35.7 | 32.3 | 0.0 |
| 5 | "Jel-5"[5] | 46.6 | 37.2 | 7.6 |
| 6 | "PTM-45"[6] | 35.0 | 31.0 | 11.4 |
| 7 | "Super-12"[7] | 109.9 | 72.2 | 76.3 |
| 8 | "Rexillium III"[8] | 74.8 | 45.6 | 26.2 |
| 9 | "Premium Talladium"[9] | 76.6 | 54.6 | 23.3 |
| 10 | "Alloy No. 1"[10] | 105.2 | — | — |

Notes for entries in TABLE V:
*Cohesive failure within the porcelain occurred for all five samples tested.
**Adhesive failure of the bond occurred for three of five samples tested.
— = Not tested.
[1]"Trubyte Bioform" silica:feldspar:alumina porcelain anterior teeth (York Division of Dentsply International).
[2]Thermocycled after bonding 500 times over a one week period between temperatures of 10° C. and 50° C.
[3]Immersed in water at 37° C. for one week instead of one day.
[4]An 84.8% Pd alloy (Unitek).
[5]A 53.5:38.9 Pd:Ag alloy (Jelenko Dental Health products).
[6]A 45:40:5 Au:Pd:Ag alloy (Jelenko Dental Health Products).
[7]An alloy of undetermined composition (Dental Alloy Products, Inc.).
[8]A 74–78:12–15:4–6:≦1.8 Ni:Cr:Mo:Be alloy (Jeneric Industries, Inc.).
[9]A metal alloy base for porcelain/metal crowns (Talladium, Inc.).
[10]A metal alloy base for porcelain/metal crowns (Matco).

This example illustrates that the priming solutions of the invention enhance adhesion to a variety of commonly-used dental substrates. On porcelain, initial results were comparable to the result obtained using the higher silane content comparison silane primer, with cohesive failure within the porcelain being observed in all samples. The silanol priming solution of the invention was less water-sensitive than the comparison silane primer, and had much better adhesion to dental alloys. Dental alloy adhesion tended to increase with a reduction in precious metal content.

The comparison silane primer could be brought within the scope of this invention through a simple modification of its ingredients. For example, sufficient aqueous acid (e.g., distilled vinegar) could be added to it to ensure that the silane becomes fully hydrolyzed in solution, coincident with attainment of the desired degree of storage stability.

EXAMPLE 7

Run no. 1 of EXAMPLE 6 was repeated using the silanol priming solution of run no. 5 of EXAMPLE 5. The average measured shear bond strength was 154.8. Cohesive failure of the porcelain occurred for each sample. However, after storage of the priming solution for nine months at room temperature, adhesive failure of the bond occurred in two out of four samples tested. Reducing the pH of this priming solution should make it storage stable (see run no. 5 of TABLE III).

EXAMPLE 8

In a series of runs, varying amounts of several solvents (run nos. 1-24) and comparison solvents (run nos. 25-40) were combined using the method of EXAMPLE 1 with varying amounts of water, 1 percent A-174 silane, and sufficient glacial acetic acid to provide a pH of 4.5 in the final mixture. The resulting priming solutions were stored at 60° C. and observed periodically. Set out below in TABLE VI are the run number, percent water, type and percent solvent, the number of days during which the priming solution remained non-hazy and the elapsed time to the onset of slight haze or haze.

TABLE VI

| Run no. | % Water | Solvent | % Solvent | No. of days non-hazy | Elapsed time to onset of slight haze or haze, days | |
|---|---|---|---|---|---|---|
| | | | | | Slight haze | haze |
| 1 | 65 | ethanol | 34 | >10 | — | — |
| 2 | 49 | ethanol | 50 | >10 | — | — |
| 3 | 39 | ethanol | 60 | >10 | — | — |
| 4 | 29 | ethanol | 70 | >10 | — | — |
| 5 | 65 | n-propanol | 34 | >10 | — | — |
| 6 | 49 | n-propanol | 50 | >10 | — | — |
| 7 | 39 | n-propanol | 60 | >10 | — | — |
| 8 | 29 | n-propanol | 70 | >10 | — | — |
| 9 | 65 | isopropanol | 34 | >10 | — | — |
| 10 | 49 | isopropanol | 50 | >10 | — | — |
| 11 | 39 | isopropanol | 60 | >10 | — | — |
| 12 | 29 | isopropanol | 70 | >10 | — | — |
| 13 | 65 | tert-butanol | 34 | 1 | 2 | 4 |
| 14 | 49 | tert-butanol | 50 | >10 | — | — |
| 15 | 39 | tert-butanol | 60 | >10 | — | — |
| 16 | 29 | tert-butanol | 70 | >10 | — | — |
| 17 | 65 | Methyl Cellosolve | 34 | 1 | 2 | 2 |
| 18 | 49 | Methyl Cellosolve | 50 | 1 | 2 | 2 |
| 19 | 39 | Methyl Cellosolve | 60 | 1 | 2 | 2 |
| 20 | 29 | Methyl Cellosolve | 70 | 5 | 6 | 6 |
| 21 | 65 | acetone | 34 | 1 | 2 | 2 |
| 22 | 49 | acetone | 50 | 2 | 3 | 3 |
| 23 | 39 | acetone | 60 | 4 | 5 | 6 |
| 24 | 29 | acetone | 70 | >10 | — | — |
| 25 | 65 | methanol | 34 | 2 | 3 | 3 |
| 26 | 49 | methanol | 50 | >10 | — | — |
| 27 | 39 | methanol | 60 | >10 | — | — |
| 28 | 29 | methanol | 70 | >10 | — | — |
| 29 | 65 | t-pentyl alcohol | 34 | <1 | 1 | 1 |
| 30 | 49 | t-pentyl alcohol | 50 | <1 | 1 | 1 |
| 31 | 39 | t-pentyl alcohol | 60 | <1 | 1 | 1 |
| 32 | 29 | t-pentyl alcohol | 70 | <1 | 1 | 1 |
| 33 | 65 | Ethyl Cellosolve | 34 | 1 | 2 | 2 |
| 34 | 49 | Ethyl Cellosolve | 50 | 1 | 2 | 2 |
| 35 | 39 | Ethyl Cellosolve | 60 | 1 | 2 | 2 |
| 36 | 29 | Ethyl Cellosolve | 70 | 1 | 2 | 2 |
| 37 | 65 | tetrahydrofuran | 34 | <1 | 1 | 1 |
| 38 | 49 | tetrahydrofuran | 50 | 1 | 2 | 2 |
| 39 | 39 | tetrahydrofuran | 60 | 1 | 2 | 2 |
| 40 | 29 | tetrahydrofuran | 70 | 1 | 2 | 6 |

Storage at 60° C. for ten days appears to be equivalent to storage at room temperature for about 120 days. This example illustrates the use of several solvents to make priming solutions which should be free from haze for at least 45 days when stored at room temperature.

EXAMPLE 9

A young adult female patient presented with a chipped porcelain crown located in the #6 position of the lower right quadrant. The chipped area was located on the labial surface of the crown, extended five mm from the base and was about four mm in diameter. A small portion (approximately one mm in diameter) of the underlying crown metal was exposed at the base. An initial repair attempt using a dental adhesive and microfilled restorative but no silanol priming solution had failed after a period of one month. The repair was repeated using the silanol priming solution of run no. 3 of EXAMPLE 5 and the following procedure.

The chipped surface was cleaned with a slurry of pumice and water. The chipped surface and a surrounding area extending two mm beyond the margins were roughened with a diamond bur. Gelled 37% orthophosphoric acid was applied to the roughened surface for 60 seconds followed by a 45 second water rinse and a thorough air dry. A thin layer of the silanol priming solution was applied with a sponge and gently dried with air until it lost its glossy appearance. Light Cured Scotchbond dental adhesive was then applied, gently dried with air and cured for ten seconds with a Visilux dental curing light. A light cured posterior restorative ("P-30" Resin Bonded Ceramic, yellow shade, 3M) was then used to fill the chipped area and cured for 30 seconds. The resotration was finished and polished using a series of abrasive disks. Both patient and dentist were satisfied with the results.

EXAMPLE 10

An adult male patient presented with a broken porcelain crown located in the #1 position of the lower right quadrant. The crown had failed at its attachment to the supporting tooth stump. Flanking the stump were two intact porcelain crowns. Due to the small size of the stump, recementation of the crown was unsuccessful. As an alternative to fabrication of a bridge, the broken crown was recemented, and splinted to the two adjacent intact crowns with the silanol priming solution used in EXAMPLE 9.

Before recementing the crown, its lingual, labial, and both interproximal surfaces were roughened with a diamond bur. The interproximal and lingual surfaces of the adjacent crowns were also roughened. The broken crown was cemented in place using an autocured quartz filled composite ("Concise" composite, 3M) and allowed to harden. The roughened surfaces of the three crowns were etched with gelled 37% orthophosphoric acid for 60 seconds, rinsed with water for 45 seconds, and dried with air. The silanol priming solution was applied with a sponge and dried with air until it lost its glossy appearance. Light Cured Scotchbond dental adhesive was then applied, gently dried with air and cured for ten seconds with a Visilux dental curing light. Using a yellow shade of Silux restorative, three quarters of each interproximal space was filled with restorative and feathered out over a two mm wide region of the labial surface of each crown. A small gap was left at the base of each interproximal area to allow for flossing. The restorative was cured for 20 seconds. More restorative was placed across the entire lingual surface of the repaired crown and feathered out over a four mm wide region of the lingual surfaces of the two adjacent crowns. The restorative was cured for twenty seconds, then contoured and polished with a series of abrasive disks. This resulted in formation of a three unit restorative veneer on the lingual surfaces of the three crowns. By yanking firmly on the middle crown it was determined that it was firmly cemented and bonded in place. Both patient and dentist were pleased with the results.

EXAMPLE 11

A young adult male patient presented with failures on all labial porcelain facings of a three unit anterior bridge. Teeth #9 and #10 had saucer-shaped failures entirely in the porcelain near the incisal edge. Tooth #8 lost enough porcelain to expose metal on the distal incisal third of the crown. The failures were probably caused by flexing of the bridge. Using the silane priming solution used in EXAMPLE 9, teeth #9 and #10 were restored during a first appointment followed by repair of tooth #8 during a second appointment.

The bridge repair began by pumicing the teeth and drilling a hole in the metal of tooth #8 for mechanical retention. All porcelain margins were bevelled with a diamond bur. The prepared surfaces were etched with gelled 37% orthophosphoric acid for one minute, rinsed with water and thoroughly dried with air. The silanol priming solution was applied using a sponge and dried with air until it lost its glossy appearance. Next, Light Cured Scotchbond dental adhesive was applied, dried with air and cured for ten seconds. A matching shade of Silux restorative was applied, cured and polished to complete the repair.

The final result was esthetic and met the needs of both the patient and dentist.

Various modifications and alterations of this invention will become apparent to those skilled in the art without departing from the scope and spirit of this invention, and it should be understood that this invention is not limited to the illustrative embodiments set forth herein.

I claim:

1. A method for priming a dental material comprising the steps of:
   (a) applying to said material a liquid layer of acidic, non-hazy, silanol priming solution comprising:
      (i) substantially fully hydrolyzed organofunctional silanol,
      (ii) water, and
      (iii) volatile alcohol or ketone solvent, said solvent being miscible with water in all proportions, having between two and four carbon atoms, and having a boiling point between about 50° and 125° C.,
      said solution containing a sufficiently low amount of silanol and sufficiently high amounts of solvent and acid to have a priming strength in excess of the cohesive strength of dental porcelain after storage of said solution at room temperature for at least about 45 days, and
   (b) allowing said layer to dry.

2. A method according to claim 1, wherein said silanol is monomeric and contains at least one non-hydrolyzable polymerizable vinyl, acryl, methacryl, glycidyl, allyl, or styryl group.

3. A method according to claim 1, wherein said silanol has the formula $R_nSi(OH)_{4-n}$ wherein R is a nonhydrolyzable polymerizable organic group and n is one to three.

4. A method according to claim 1, wherein said silanol comprises hydrolyzed gamma-methacryloxypropyltrimethoxysilane.

5. A method according to claim 1, wherein said solution contains about 0.5 to about five weight percent of said silanol.

6. A method according to claim 5, wherein said solution contains about 0.5 to about 1.5 weight percent of said silanol.

7. A method according to claim 1, wherein said solution contains at least 35 weight percent of said solvent and said solvent comprises ethanol.

8. A method according to claim 7, wherein said solution contains at least about 50 weight percent of said ethanol.

9. A method according to claim 7, wherein said solution contains about 70 to about 99 weight percent of said ethanol.

10. A method according to claim 1, wherein said solution contains at least about 50 weight percent of said solvent and said solvent comprises n-propanol or isopropanol.

11. A method according to claim 1, wherein said solution contains at least about 60 weight percent of said solvent and said solvent comprises tert-butanol.

12. A method according to claim 1, wherein said solution contains at least about 70 weight percent of said solvent and said solvent comprises 2-methoxyethanol or acetone.

13. A method according to claim 1, wherein said solution has a pH between about two and about six.

14. A method according to claim 1, wherein said solution has a pH between about three and about five.

15. A dental article, suitable for use in the mouth, comprising a dental material having thereon a liquid layer of acidic, non-hazy, silanol priming solution comprising:
   (i) substantially fully hydrolyzed organofunctional silanol,
   (ii) water, and
   (iii) volatile alcohol or ketone solvent, said solvent being miscible with water in all proportions, having between two and four carbon atoms, and having a boiling point between about 50° and 125° C., said solution containing a sufficiently low amount of silanol and sufficiently high amounts of solvent and acid to have a priming strength in excess of the cohesive strength of dental porcelain after storage of said solution at room temperature for at least about 45 days.

16. A dental article according to claim 15, wherein said silanol comprises hydrolyzed gamma-methacryloxypropyltrimethoxysilane, said solvent comprises ethanol, and said solution contains about 0.01 to about nine weight percent of said silanol and has a pH below about six.

17. A dental article according to claim 16, wherein said dental material comprises feldspathetic, nepheline synenite, alumina-base, or synthetic dental porcelain.

18. A dental article according to claim 16, wherein said dental material comprises dental metal or alloy comprising gold, silver, platinum, palladium, chromium, or nickel.

19. A dental article according to claim 16, wherein said dental material comprises a crown or bridge.

20. A one-part liquid silanol priming composition, useful in dentistry, comprising an acidic, non-hazy solution consisting essentially of (i) substantially fully hydrolyzed organofunctional silanol,
(ii) water, and
(iii) ethanol, said solution containing a sufficiently low amount of silanol and sufficiently high amounts of ethanol and acid to have a priming strength in excess of the cohesive strength of dental porcelain after storage of said solution at room temperature for at least about 45 days.

21. A composition according to claim 20, wherein said silanol comprises hydrolyzed gamma-methacryloxypropyltrimethoxysilane, and said solution contains about 0.01 to about nine weight percent of said silane, at least about 50 weight percent of said ethanol, and has a pH below about six.

22. A composition according to claim 21, wherein said solution contains about 0.5 to about 1.5 weight percent of said silane, about 70 to about 99 weight percent of said ethanol, and has a pH of about three to about five.

* * * * *